(12) United States Patent
Huang et al.

(10) Patent No.: US 8,603,785 B2
(45) Date of Patent: Dec. 10, 2013

(54) METHOD OF ORGANIC POLYMER DEGRADATION BY DIHYDROLIPOAMIDE DEHYDROGENASE

(75) Inventors: Shir-Ly Huang, Taoyuan (TW); Yu-Ling Sun, Taoyuan (TW)

(73) Assignee: National Central University, Johngli (TW)

( * ) Notice: Subject to any disclaimer, the term of this patent is extended or adjusted under 35 U.S.C. 154(b) by 514 days.

(21) Appl. No.: 11/902,077

(22) Filed: Sep. 18, 2007

(65) Prior Publication Data
US 2008/0166778 A1    Jul. 10, 2008

(30) Foreign Application Priority Data
Nov. 30, 2006   (TW) .............................. 095144557 A

(51) Int. Cl.
| | | |
|---|---|---|
| *C12P 7/00* | (2006.01) | |
| *C12P 21/04* | (2006.01) | |
| *C12P 21/06* | (2006.01) | |
| *C12Q 1/68* | (2006.01) | |
| *C12N 1/20* | (2006.01) | |
| *C12N 15/00* | (2006.01) | |
| *C12N 9/04* | (2006.01) | |
| *C12N 5/00* | (2006.01) | |
| *C07H 21/04* | (2006.01) | |

(52) U.S. Cl.
USPC ...... 435/132; 435/6.1; 435/252.3; 435/320.1; 435/190; 435/440; 435/69.1; 435/71.1; 435/325; 536/23.2; 536/23.4

(58) Field of Classification Search
USPC ....................................... 435/132, 190, 252.3
See application file for complete search history.

(56) References Cited

PUBLICATIONS

Hung et al. An oxygen consumption enzyme involved in bacterial stress response when grown on non-ionic surfactants. FEBS Journal, (Jul. 2005) vol. 272, No. Suppl. 1, pp. 425.*
Sun et al. Thesis 942204004—defended on Jul. 19, 2006 and deposited on Jul. 24, 2006—English Traslation—pp. 1-8.*
Protein Purification. Handbook. Amersham Pharmacia Biotech. 1999. 1-94.*
Novagen Catalog—Protein Expression—2001.*
Branden et al. Introduction to Protein Structure, Garland Publishing Inc., New York, p. 247, 1991.*

* cited by examiner

*Primary Examiner* — Yong Pak
(74) *Attorney, Agent, or Firm* — Jackson IPG PLLC

(57) ABSTRACT

A dihydrolipoamide dehydrogenase (DLD) in a germ is recombined. The new DLD is applied in a solution to degrade an ether bond of an organic polymer. With the present invention, bioremediation is accomplished without secondary pollution of compounds which have environmental hormones.

11 Claims, 6 Drawing Sheets

| | | | | |
|---|---|---|---|---|
| 1 | atgggcagca | gccatcatca | tcatcatcac | agcagcggcc | tggtgccgcg |
| 51 | cggcagccat | atggctagca | tgactggtgg | acagcaaatg | ggtcgcggat |
| 101 | ccgaattcat | gagccataaa | ttcgacgtgg | ttgtgattgg | tgccggcccc |
| 151 | ggcggctacg | tagccgccat | ccgtgccgcc | caactcggcc | tgaagaccgc |
| 201 | ttgcatcgag | aagtacatcg | gtaaagaggg | caaggtcgct | ctcggcggta |
| 251 | cctgcctgaa | cgtaggctgc | attccgtcca | aggcgctgct | ggacagctcc |
| 301 | tggaagtaca | aggaagccaa | agaaggtttc | gagattcacg | gtatctccac |
| 351 | cggcggcgtg | aagatggacg | tcccggcgat | ggttgcccgc | aaggccaaca |
| 401 | tcgtgaagaa | cctgaccggc | ggcatcgcta | ccctgttcaa | ggccaacggc |
| 451 | gtgacttcct | tcgaaggcca | cggcaaggtc | ctggccaaca | agcaggtcga |
| 501 | agtgaccggc | ctggacggca | agacccaggt | gttggaagcc | gacaacatca |
| 551 | tcatcgcctc | gggctcccgt | ccggtggaaa | tcccgccggc | tccgctgacc |
| 601 | gaagacgtga | ttgtcgattc | caccggcgcc | ctggaattcc | agagcgtacc |
| 651 | caagaagctg | ggcgtgatcg | gtgctggcgt | tatcggcctg | gaactgggtt |
| 701 | cggtctgggc | tcgcctgggc | gctgaagtca | ccgtcctgga | agccctggac |
| 751 | aagttcctcc | cggctgccga | cgagcagatc | gccaaggaag | cgctgaagac |
| 801 | cctgaccaag | caaggcctga | acatccgcct | gggcgctcgc | gtcaccggtt |
| 851 | cggaagtgaa | gaagaagcag | gtcaccgtgg | ccttcaccga | tgccaacggc |
| 901 | gagcagaagg | aaaccttcga | caagctgatc | gtggccgtgg | ccgtcggcc |
| 951 | ggtgaccacc | gatctgctgg | ctgcggacag | cggcgtgacc | ctggacgagc |
| 1001 | gcggtttcat | ctacgtcgac | gaccactgca | agaccagcgt | tccgggcgtc |
| 1051 | tacgccatcg | gtgatgtggt | ccgtggcgcc | atgctggcgc | acaaggcctc |
| 1101 | ggaagagggc | gtgatggttg | ccgagcgcat | cgccggccac | aaggcccaga |
| 1151 | tgaactacga | cctgattccg | tcggtgatct | acacccaccc | ggaaatcgca |
| 1201 | tgggtcggca | agaccgagca | gcagctcaag | ggcgaaggcg | tcgaagtcaa |
| 1251 | cgtcggcacc | ttcccgttcg | ccaccagcgg | ccgcgccatg | gctgccaacg |
| 1301 | acaccggcgg | cctggtcaaa | gtcatcgccg | atgccaagac | cgaccgcgta |
| 1351 | ctgggcgtcc | acgtgatcgg | cccgagcgcc | gccgagctgg | ttcagcaggg |
| 1401 | cgcgatcggc | atggaattcg | gcaccagtgc | cgaagacctg | ggcatgatgg |
| 1451 | tcttctccca | cccgactctg | tccgaagcgc | tgcacgaagc | ggcactggca |
| 1501 | gtgaatggcc | acgccatcca | catcgccaac | cgaaagaagc | gcctcgagca |
| 1551 | ccaccaccac | caccactag | | | |

FIG. 2

METHOD OF ORGANIC POLYMER DEGRADATION BY DIHYDROLIPOAMIDE DEHYDROGENASE

FIELD OF THE INVENTION

The present invention relates to an organic polymer decomposition; more particularly, relates to a recombinant dihydrolipoamide dehydrogenase (DLD), then processing affinity column chromatography and gel filtration, then processing a purification to the DLD, and then applying the DLD in a solution having nicotinamide adenine dinucleotide (NADH) and ferric ions to degrade an octylphenol polyethoxylates (OPEOn).

DESCRIPTION OF THE RELATED ART

At the present time, all kinds of surfactants and organic polymers are widely used in fields of agriculture, industry and chemistry. As they are all discharged in the environment, compounds of environmental hormones, like nonylphenol and octylphenol, are produced to pollute the environment and thus damage human's health. Therefore, the whole world has paid much attention on this problem. In some bioremediation process, surfactants are usually applied to enhance biodegradation of pollutant. So, it is necessary to avoid secondary pollution produced by exogenously added surfactants having alkylphenol structures.

APEOn is a commonly used surfactant. In sediment caused by effluent water, in active sludge of water treatment plant, and even in normal living environment, compounds having short bonds, like $APEO_1$ and $APEO_2$, or having carbonate derivatives, like $APEC_1$, $APEC_2$ and alkylphenol (AP), are usually found. The above compounds are intermediate metabolites on degrading ethoxylate (EO) of the APEOn, which are hard to be degraded by microorganism in the environment. Yet these intermediate metabolites with activity of environmental hormones, which are accumulated crucial in polluting the environment.

OPEOn belongs to APEOn, which has an octylphenyl moiety connected with 9.5 units average number of polyethylene oxide chain. In previous studies, at least 20 degrading bacteria are isolated which uses OPEOn as a sole carbon source, like *Pseudomonas putida* and *Pseudomonas* sp. However, it is not yet known whether those specific bacteria which use OPEOn as a sole carbon source would accumulate intermediates with environmental hormone activity, such as $APEO_1$ and alkylphenol. Hence, the prior art does not fulfill users' requests on actual use.

SUMMARY OF THE INVENTION

The main purpose of the present invention is to cut an ether bond of an organic polymer by DLD in a proper environment.

Another condition of the present invention is to add NADH or NADPH and ferric ions to a solution for the DLD to cut the ether bond of the organic polymer.

To achieve the above purpose, the present invention is a method of an organic polymer decomposition by using a DLD, where the gene of DLD is recombined in *Escherichia coli* to be isolated and purified; then the DLD is applied in a solution having NADH and ferric ions; and then a mass spectrometer is used for an analysis to show that the DLD shortens the length of ethoxylate of OPEOn, where the DLD is obtained from a strain of *Pseudomonas nitroreducens* TX1 (deposited at ATCC, PTA-6168) which is patented by Taiwan Patent (I 240001) and US patent (U.S. Pat. No. 7,115,411 issued to the applicant); the DLD is purified to a degree of >95% purity; and the DLD in the solution has an oxygen-consuming activity between 100 and 200 nmole/min per gram of enzyme. Accordingly, a novel method of organic polymer decomposition by using a DLD is obtained.

BRIEF DESCRIPTIONS OF THE DRAWINGS

The present invention will be better understood from the following detailed description of the preferred embodiment according to the present invention, taken in conjunction with the accompanying drawings, in which FIG. 1 is the flow chart showing the preferred embodiment according to the present invention;

FIG. 2 is the complete gene sequence of the recombinant DNA (SEQ ID NO:1) from *Pseudomonas nitroreducens* TX1 and expressed in *E. coli*.;

DESCRIPTION OF THE PREFERRED EMBODIMENT

The following description of the preferred embodiment is provided to understand the features and the structures of the present invention.

Figure 1:
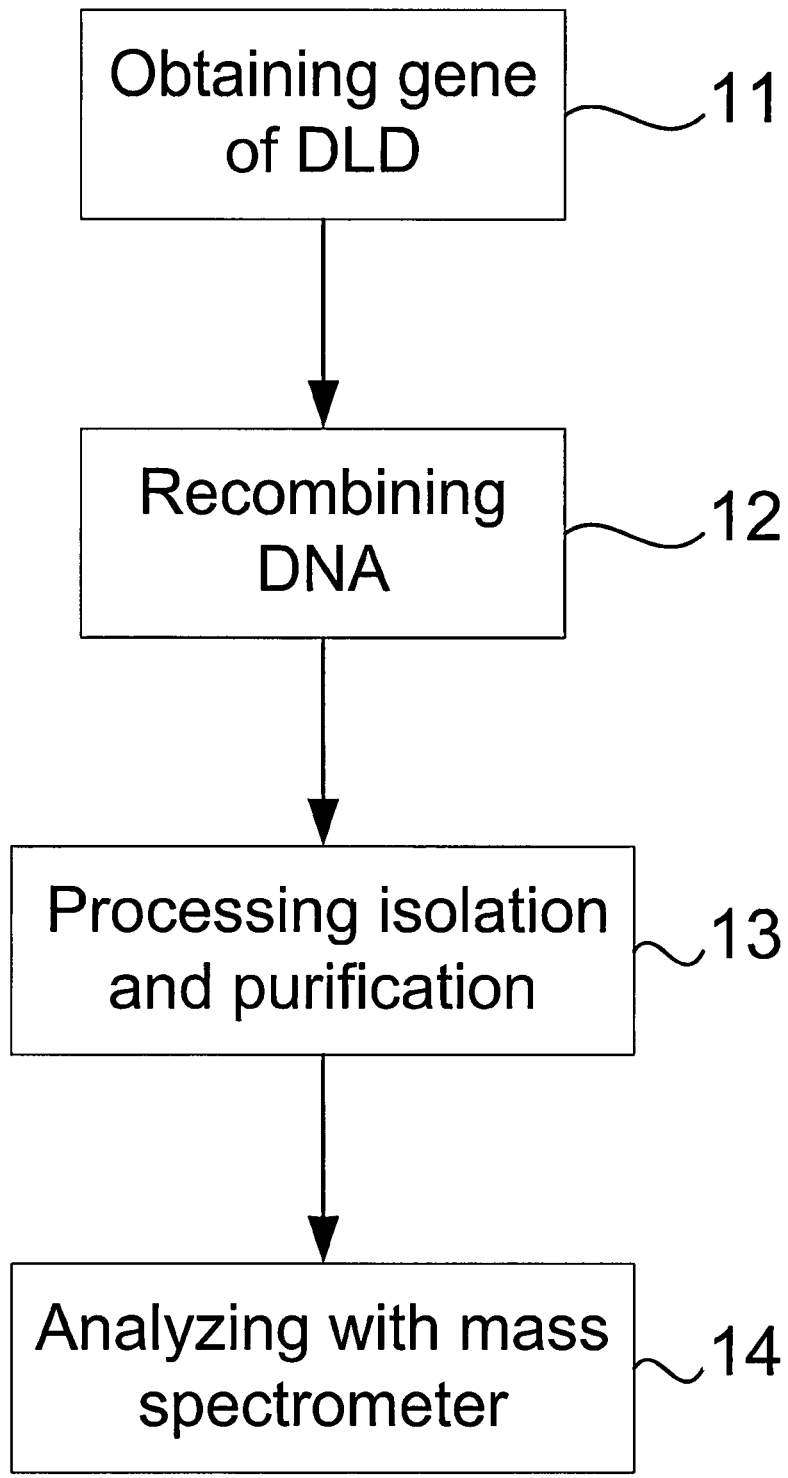

Please refer to FIG. 1, which is a flow view showing a preferred embodiment according to the present invention. As shown in the figure, the present invention is a method of organic polymer decomposition by using a dihydrolipoamide dehydrogenase (DLD), comprising the following steps:

(a) Obtaining gene of DLD 11: A gene of a DLD is obtained from a strain of *Pseudomonas nitroreducens* TX1.

(b) Recombining DNA 12: By recombining the DLD gene and fused to a vector for expression as a tag fusion protein in *E. coli*.

(c) Processing isolation and purification 13: Through a 2-step column chromatography of affinity and gel filtration, purification of DLD is processed, where the DLD is purified to a degree of >95%.

(d) Analyzing with mass spectrometer 14: A solution having nicotinamide adenine dinucleotide (NADH) and ferric ions is obtained to be dissolved with the DLD. Then the solution is analyzed with a liquid chromatograph-mass spectrometer (LC-MS) to identify the degradation products from OPEOn, where the NADH is nicotinamide-adenine dinucleotide or nucotinamide-adenine dinucleotide phosphate (NATPH); the NADH (or NADPH) has a molecular concentration between 0.1 and 10 millimoles (mmol); the ferric ion has a concentration between 0.1 and 2.0 mM; the DLD in the solution has an oxygen-consuming activity between 100 and 200 nmole/min per gram of enzyme; and the target compounds are alkylphenol polyethoxylates (APEOn), dodecyl octaethoxylate, polyethylene glycol, 1,4-dioxane, trioxane or cyclic ether. When there is excess of NADH, the DLD produces hydrogen peroxide ($H_2O_2$) and reduces ferric ions into ferrous ions. And, when the hydrogen peroxide and the ferrous ion are co-existed, a Fenton reaction happens to produce a hydroxyl radical (.OH) and the hydroxyl radical attacks an ethoxylate ether bond of the OPEOn to decompose the bond by shortening the length of ethoxylate chain.

Please refer to FIG. 2, which is a gene sequence of DLD from *Pseudomonas nitroreducens* TX1. As shown in the figure, gene sequence of DLD from *Pseudomonas nitroreducens* TX1 is shown in italic letters; two sections of the first framed letters is a beginning and transcription; and two sections of underlined letters for obtaining a fusion protein, where each section of underlined letters has six tags of histidine. And the part of gene sequence is the product obtained after recombining the DNA.

Figure 3:
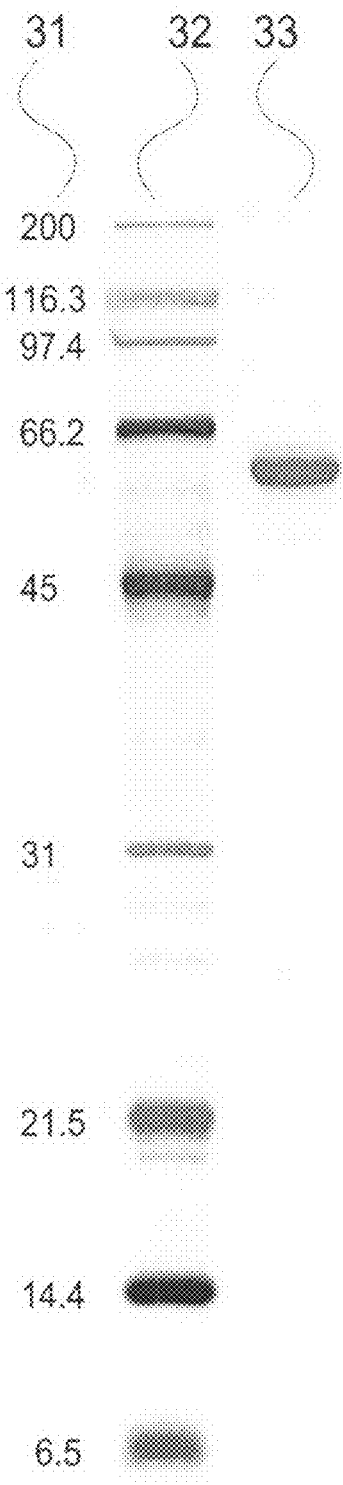
FIG. 3 is the graph showing the SDS-polyacrylamide gel electrophoresis analysis of purified DLD.

Please refer to FIG. 3, which is a view showing a 12% SD S-PAGE analysis of purified recombinant DLD. As shown in the figure, after recombining DNA with DLD gene, an analysis of sodium dodecyl sulfate polyacryl amide gel electrophoresis (SDS-PAGE) to a purified DLD is processed. Accompanied with molecular weight (mol wt in kDa) marker labeled 31, a purified recombinant DLD 33 according to the present invention is analyzed by comparing to mol wt marker proteins 32, where mol wt of myosin is 200 kDa; β-galactosidase, 116.2 kDa; phosphorylase b, 97.4 kDa; bovine serum albumin, 66.2 kDa; ovalbumin, 45 kDa; carbonic anhydrase, 31 kDa; trypsin inhibitor, 21.5 kDa; lysozyme, 14.4 kDa; and aprotinin, 6.5 kDa.

Figure 4:
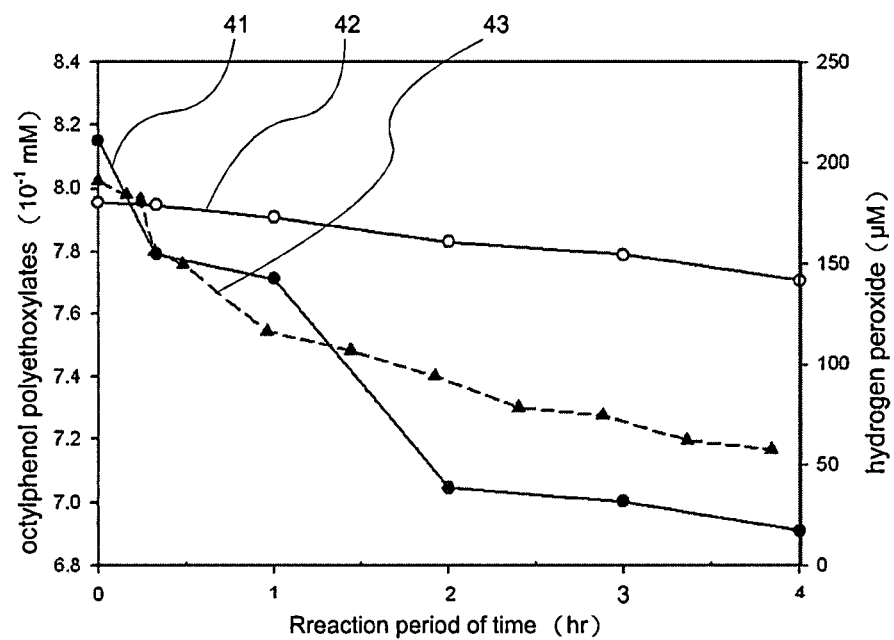
FIG. 4 is the graph showing the degradation of OPEOn by the purified DLD.

Please refer to FIG. 4, which is a view showing a degradation of OPEOn by DLD. As shown in the figure, the quantity of OPEOn treated with a purified recombinant DLD 41 OPEOn quantity without the addition of purified recombinant DLD 42, and a hydrogen peroxide 43 produced are compared.

Figure 5A:
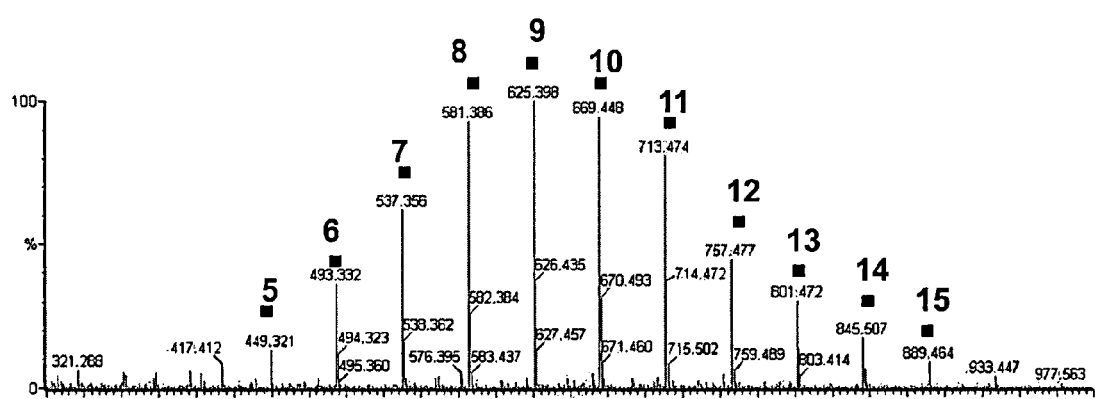
FIG. 5A and FIG. 5B are the graphs showing the mass spectra of products obtained through the degradation of OPEOn by the DLD.
Figure 5B:
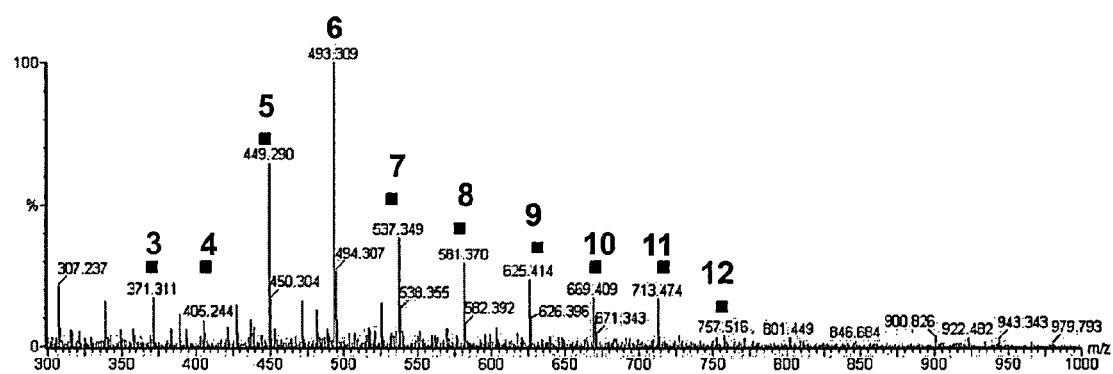

Please refer to FIG. 5A and FIG. 5B, which are views showing mass spectra of products obtained through degradation of OPEOn by the DLD. FIG. 5A shows a status of catalyzing an OPEOn on 0 minute (min); and FIG. 5B shows a status of catalyzing the OPEOn on 120 min. The numbers on the figures represent numbers of units of EO of OPEOn.

In summary, the present invention is a method of an organic polymer decomposition by using a DLD, where, in a certain environment, DLD is applied to cut an ether bond of an organic polymer.

The preferred embodiment herein disclosed is not intended to unnecessarily limit the scope of the invention. There fore, simple modifications or variations belonging to the equivalent of the scope of the claims and the instructions disclosed herein for a patent are all within the scope of the present invention.

What is claimed is:

1. A method of severing an ether bond in octylphenol polyethoxylates (OPEOn) by using dihydrolipoamide dehydrogenase (DLD), comprising the steps of:
   (a) obtaining a gene of DLD from a strain of *Pseudomonas nitroreducens* TX1;
   (b) recombining said gene of DLD by inserting said gene of DLD into a vector for expression as a tag fusion protein in *Escherichia coli* to obtain a recombinant DLD encoded by the sequence of SEQ ID NO:1;
   (c) processing an isolation step and a purification step of said recombinant DLD through column chromatography by affinity and gel filtration to result in a purified DLD; and
   (d) adding said purified DLD to a solution of octylphenol polyethoxylates (OPEOn), allowing said severing of said ether bond.

2. The method according to claim 1, wherein said purified DLD in said solution has an oxygen-consuming activity between 100 and 200 nanomoles per minute (nmole/min).

3. The method according to claim 1, wherein said purified DLD has a purity of greater than 95 percent.

4. The method according to claim 1, wherein said solution has reduced nicotinamide adenine dinucleotide (NADH) or nicotinamide-adenine dinucleotide phosphate (NADPH) and ferric ions.

5. The method according to claim 4, wherein said NADH (or NADPH) has a molecular concentration between 0.1 and 10 millimoles (mmol).

6. The method according to claim 4, wherein said ferric ion has a concentration between 0.1 and 2.0 mM.

7. The method according to claim 1, wherein said ether bond is ethoxylate (EO); and wherein said OPEOn is selected from a group consisting of Alkylphenol polyethoxylates (APEOn), dodecyl octaethoxylate, polyethylene glycol, 1,4-dioxane, trioxane and cyclic ether.

8. The method according to claim 1, wherein said fusion protein has six tags of histidine.

9. A method of obtaining octylphenol polyethoxylates (OPEOn) having a severed ether bond, comprising the steps of:
   (a) producing the recombinant DLD fusion gene of SEQ ID NO:1, having six tags;
   (b) expressing the fusion protein in *E. coli*;
   (c) purifying the DLD fusion protein using tag affinity chromatography and gel filtration;
   (d) combining the purified DLD with octylphenol polyethoxylates ($OPEO_n$), 0.1 to 10 mM NADH or NADPH and 0.1 to 2.0 mM ferric ions to sever the ether bond; and
   (e) isolating the severed $OPEO_n$.

10. The method according to claim 9, wherein said ether bond is ethoxylate (EO); and wherein said OPEOn is chosen from Alkylphenol polyethoxylates (APEOn), dodecyl octaethoxylate, polyethylene glycol, 1,4-dioxane, trioxane and cyclic ether.

11. The method of claim 9, wherein the DLD fusion protein is purified to at least 95% purity.

* * * * *

```
                        SEQUENCE LISTING

<160> NUMBER OF SEQ ID NOS: 1

<210> SEQ ID NO 1
<211> LENGTH: 1545
<212> TYPE: DNA
<213> ORGANISM: Artificial
<220> FEATURE:
<223> OTHER INFORMATION: A recombinant Dihydrolipoamide Dehydrogenase
      from Pseudomonas nitroreducens TX1 and expressed in E. Coli.

<400> SEQUENCE: 1
atgggcagca gccatcatca tcatcatcac agcagcggcc tggtgccgcg cggcagccat      60
atggctagca tgactggtgg acagcaaatg ggtcgcggat ccgaattcat gagccataaa     120
ttcgacgtgg ttgtgattgg tgccggcccc ggcggctacg tagccgccat ccgtgccgcc     180
caactcggcc tgaagaccgc ttgcatcgag aagtacatcg gtaaagaggg caaggtcgct     240
ctcggcggta cctgcctgaa cgtaggctgc attccgtcca aggcgctgct ggacagctcc     300
tggaagtaca aggaagccaa agaaggtttc gagattcacg gtatctccac cggcggcgtg     360
aagatggacg tcccggcgat ggttgcccgc aaggccaaca tcgtgaagaa cctgaccggc     420
ggcatcgcta ccctgttcaa ggccaacggc gtgacttcct tcgaaggcca cggcaaggtc     480
ctggccaaca agcaggtcga agtgaccggc ctggacggca gacccaggt gttggaagcc     540 gacaacatca tcatcgcctc gggctcccgt ccggtggaaa tcccgccggc tccgctgacc     600
gaagacgtga ttgtcgattc caccggcgcc ctggaattcc agagcgtacc caagaagctg     660
ggcgtgatcg gtgctggcgt tatcggcctg gaactgggtt cggtctgggc tcgcctgggc     720
gctgaagtca ccgtcctgga agccctggac aagttcctcc cggctgccga cgagcatatc     780
gccaaggaag cgctgaagac cctgaccaag caaggcctga acatccgcct gggcgctcgc     840
gtcaccggtt cggaagtgaa gaagaagcag gtcaccgtgg ccttcaccga tgccaacggc     900
gagcagaagg aaaccttcga caagctgatc gtggccgtgg gccgtcggcc ggtgaccacc     960
gatctgctgg ctgcggacag cggcgtgacc ctggacgagc gcggtttcat ctacgtcgac    1020
gaccactgca agaccagcgt tccggcgtc tacgccatcg gtgatgtggt ccgtggcgcc    1080
atgctggcgc acaaggcctc ggaagagggc gtgatggttg ccgagcgcat cgccggccac    1140
```

```
aaggcccaga tgaactacga cctgattccg tcggtgatct acacccaccc ggaaatcgca    1200
tgggtcggca agaccgagca gcagctcaag ggcgaaggcg tcgaagtcaa cgtcggcacc    1260
ttcccgttcg ccgccagcgg ccgcgccatg gctgccaacg acaccggcgg cctggtcaag    1320
gtcatcgccg atgccaagac cgaccgcgta ctgggcgtcc acgtgatcgg cccgagcgcc    1380
gccgagctgg ttcagcaggg cgcgatcggc atggaattcg gcaccagtgc cgaagacctg    1440
ggcatgatgg tcttctccca cccgactctg tccgaagcgc tgcacgaagc ggcactggca    1500
gtgaatggcc acgccatcca catcgccaac cgaaagaagc gctga                   1545
```